US010071104B2

(12) United States Patent
Glaser

(10) Patent No.: US 10,071,104 B2
(45) Date of Patent: *Sep. 11, 2018

(54) PHARMACEUTICAL COMPOSITIONS CONTAINING TESTOSTERONE AND AN AROMATASE INHIBITOR

(71) Applicant: Rebecca L. Glaser, Dayton, OH (US)

(72) Inventor: Rebecca L. Glaser, Dayton, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/248,556

(22) Filed: Aug. 26, 2016

(65) Prior Publication Data

US 2016/0361323 A1 Dec. 15, 2016

Related U.S. Application Data

(63) Continuation of application No. 12/620,725, filed on Nov. 18, 2009.

(60) Provisional application No. 61/200,867, filed on Dec. 5, 2008.

(51) Int. Cl.
| *A61K 31/568* | (2006.01) |
| *A61K 31/4196* | (2006.01) |
| *A61K 9/00* | (2006.01) |
| *A61K 9/20* | (2006.01) |
| *A61K 31/565* | (2006.01) |

(52) U.S. Cl.
CPC .......... *A61K 31/568* (2013.01); *A61K 9/0024* (2013.01); *A61K 9/2013* (2013.01); *A61K 31/4196* (2013.01); *A61K 31/565* (2013.01)

(58) Field of Classification Search
CPC ..... A61K 31/568; A61K 31/4196; A61K 9/00
See application file for complete search history.

(56) References Cited

U.S. PATENT DOCUMENTS

| 3,948,254 A | 4/1976 | Zaffaroni |
| 5,035,891 A | 7/1991 | Runkel et al. |
| 2001/0041697 A1 | 11/2001 | Foster et al. |
| 2004/0235812 A1 | 11/2004 | Caspers |
| 2007/0196421 A1 | 8/2007 | Hunter et al. |
| 2008/0161355 A1 | 7/2008 | Curry et al. |
| 2009/0215731 A1 | 8/2009 | Birrell |
| 2009/0318398 A1 | 12/2009 | Dudley et al. |

FOREIGN PATENT DOCUMENTS

| GB | 2154138 | 9/1985 |
| GB | 2167662 | 6/1986 |
| JP | 59-044310 | 3/1984 |
| WO | 98/40075 | 9/1998 |
| WO | 2005/011705 | 2/2005 |
| WO | 2007/026138 | 3/2007 |
| WO | 2007/045027 | 4/2007 |

OTHER PUBLICATIONS

PCT, International Search Report and Written Opinion, International Application No. PCT/US2009/065458 (8 pages) (Jan. 15, 2010).
Product information, "Testopel® Pellets," Bartor Pharmacal, Rye, NY (4 pages) (Jan. 2009).
Nash, H. et al., "Steroid Release From Silastic Capsules and Rods," *Contraception*, 18, 367-394 (1978).
Shippy et al., "Controlled Release of Testosterone Using Silicone Rubber," *J. Biomed. Mater. Res.*, 7, 95-110 (1973).
Handelsman, D.J. et al., "Pharmacokinetics and Pharmacodynamics of Testosterone Pellets in Man," *Journal of Clinical Endocrinology & Metabolism*, vol. 71, No. 1, pp. 216-222 (1990).
Web page featuring "Testosterone Implants 24 mg, Testosterone Implants 200 mg," presented by Malahyde Information Systems, http://home.intekorn.com/pharm/donmed/test-imp.html (1987).
"Pellets—Hormone Implants FAQ," http://www.hormonebalance.org/files/Web%20Pellets%20Handout.doc (date of first publication unknown).
Birrell, S.N. et al., "Testosterone undecanoate treatment reduces joint morbidities induced by anastrozole therapy in postmenopausal women with breast cancer: results of a double-blind, randomized phase II trial," Poster Discussion 8, No. 804 ( 2009).
PCT, International Preliminary Report on Patentability, International Application No. PCT/US2009/065458 (dated Jun. 16, 2011).
EP, Search Report, European Application No. 09830879.4 (dated May 7, 2012).
Kelleher, S. et al., "Testosterone release reate and duration of action of testosterone pellet implants," *Clinical Endocrinology* (2004), 60, pp. 420-428.
Behre et al. Testosterone : action, deficiency, substitution, 3rd. Edition, 2004, Chapter 14, pp. 405-444.
Plourde et al. J. of Steroid Biochem. Mol. Biol., 1995, Abstract.
Rathbone et al. Controlled Release Veterinary Drug Release, Elevier, Jul. 2000, pp. 36-38.

*Primary Examiner* — Samira Jean-Louis
(74) *Attorney, Agent, or Firm* — Alicia M. Passerin, Esq.; Leech Tishman Fuscaldo & Lampl

(57) ABSTRACT

An implant comprising testosterone or an ester thereof and an aromatase inhibitor; the aromatase inhibitor may be selected from the group consisting of anastrozole, letrozole, and exemestane. In one embodiment the implant is a sustained release, subcutaneous implant. Also disclosed are therapies for patients with symptoms of relative androgen deficiency, breast cancer survivors and other therapies in which testosterone is indicated but elevated estradiol levels are avoided.

19 Claims, No Drawings

PHARMACEUTICAL COMPOSITIONS CONTAINING TESTOSTERONE AND AN AROMATASE INHIBITOR

CROSS-REFERENCE TO RELATED APPLICATIONS

This application is a continuation of U.S. application Ser. No. 12/620,725, filed Nov. 18, 2009, which claims the benefit of U.S. Application Ser. No. 61/200,867, filed Dec. 5, 2008.

BACKGROUND

Testosterone, delivered by subcutaneous pellet implant has been used in the United States, Europe and Australia in both men and women to treat symptoms of testosterone deficiency. Symptoms of testosterone hormone deficiency include fatigue, lack of energy, depression, memory loss, concentration difficulties, weakness, aches, pains, anemia, suppressed immune system, insomnia, hot flashes, night sweats, bone loss (osteopenia, osteoporosis), muscle mass loss, inability to loose weight (fat mass), anxiety, emotional lability, vaginal dryness, urinary urgency, urinary frequency, and incontinence.

Potential benefits of testosterone delivery by implant include increased bone density, increased energy, relief of lethargy, relief of depression and anxiety, improved memory and concentration, improved sleep, increased muscle mass, decreased fat mass, relief of aches and pains, relief of breast pain, relief of migraine headaches, restoration of sex drive and libido, menopausal syndrome relief (hot flashes, night sweats), prevention of uterine bleeding caused by estrogens, use in dysmenorrheic patients with endometriosis or small fibroids, relief of nocturia and incontinence, relief of vaginal symptoms, arterial vaso-dilation, increased arterial blood flow, lowering the risk of breast cancer in women on estrogen/progestin therapy, palliative measure (carcinoma of the breast), decreased proliferation of breast tissue, reduction of ER (estrogen receptor) alpha, enhance immune system, and increased red blood cell production.

Anastrozole is an aromatase inhibitor and has been used orally as an adjuvant therapy in breast cancer in postmenopausal women. By blocking the enzyme "aromatase," anastrozole inhibits the conversion of testosterone to estradiol thus preventing the stimulation of breast tissue and breast cancer cells by estradiol. Oral anastrozole has been used in male patients to prevent the conversion of testosterone to estradiol, thus raising testosterone levels and lowering estradiol levels.

SUMMARY OF INVENTION

The invention relates to a pharmaceutical composition comprising testosterone or an ester thereof and an aromatase inhibitor. In one embodiment the pharmaceutical composition is formulated as a sustained release, subcutaneous pellet implant. In this composition, an aromatase inhibitor is combined with testosterone to continuously deliver testosterone and simultaneously prevent the conversion of testosterone to estradiol by the aromatase inhibitor.

The composition and, more particularly, the testosterone-anastrozole subcutaneous, sustained release implant, is indicated for use in male and female patients. It may be used in patients with symptoms of relative androgen deficiency (including bone loss, joint/muscular pain, anemia, suppressed immune system, depression, memory loss, fatigue, sexual problems and sleep problems) who may benefit from testosterone therapy, where elevated estradiol (estrogen) levels are to be avoided. In one embodiment it is indicated for use in breast cancer survivors where the use of testosterone has been cautioned against because of the aromatization of testosterone to estradiol, a potent estrogen. Estradiol is known to stimulate proliferation of breast tissue and breast cancer. It may also be indicated for patients with a diagnosis of invasive or non-invasive breast cancer (e.g., hormone receptor positive (estrogen receptor positive) breast cancer survivors); patients at high risk for breast cancer (e.g., family history of breast cancer, gene positive (BRCA I or BRCA II) for breast cancer, prior breast biopsy with 'atypia' or a diagnosis of 'atypical ductal hyperplasia,' or diagnosis of Lobular Carcinoma in Situ); patients with benign breast disease (e.g., fibrocystic breast disease, breast tenderness, cystic mastitis); obese patients (e.g., elevated aromatase (enzyme) levels are found in fat tissue making this group of patients more likely to convert testosterone to estradiol such that lowering estradiol levels may help with weight loss); male patients on testosterone therapy who have previously demonstrated elevated estrogen levels; and patients with insulin resistance (e.g., elevated estrogen has been associated with insulin resistance).

In one embodiment, an implant is composed of the active ingredients testosterone and anastrozole. In one embodiment the implant may consist of the active ingredients, however, to improve the integrity of the pellet and facilitate its manufacture in one embodiment the active ingredients are used with excipients such as a lubricant and/or a binder. In one embodiment the lubricant is stearic acid. In one embodiment the binder is povidone. In one embodiment, the excipients make up less than 20%, more particularly less than 10%, and still more particularly less than 5% of the composition. In one embodiment, these ingredients are formed into an implant such as cylindrical pellets measuring in one case approximately 3.1 mm by 6.5 mm, then packaged and sterilized. In one embodiment the implant contains the testosterone and the aromatization inhibitor in a weight ratio of about 5:1 to about 30:1 and, more particularly in a ratio of about 15:1 to 25:1 and still more particularly 10:1 to 20:1. For example in one instance the implant includes 60 mg testosterone and 6 mg inhibitor and in another instance the implant contains 60 mg testosterone and 3 mg inhibitor. Preferably the implant fits through a standard size, 3.2 mm pellet implanter (trocar/cannula) and can be inserted through a small incision into subcutaneous tissue in an area that experiences relatively little movement such as the lower abdomen or upper buttocks. In one embodiment, a single implant may be used. In another embodiment depending on the condition of the patient, two or more implants may be used together.

In one embodiment, the implant may be formulated to deliver continuous, therapeutic testosterone and anastrozole therapy for 12-16 weeks. In one embodiment, particularly when the amount of excipients is minimal, the implant provides approximately zero order release proportional to the surface area of the pellet(s).

The implant can enable significantly lower dosing (for example, 6 mg released over 100 days (0.06 mg/day) vs. 1.0 mg/d oral dose) with fewer side effects than oral anastrozole therapy (see below). In addition, avoiding the GI tract avoids nausea or adverse effects to the GI tract. Subcutaneous delivery also avoids adverse effects from 'first pass' metabolism in the liver including hepatic-toxicity or increase in clotting factors. Subcutaneous delivery of the combination of testosterone and anastrozole also can reduce or eliminate patient non-compliance.

One manifestation of the invention is a subcutaneous, sustained release pellet implant. However, other dosages such as oral tablets and capsules, and transdermal patches constitute additional embodiments of the invention.

In one embodiment, the combination of testosterone (hormone) with anastrozole (aromatase inhibitor) will elevate testosterone levels without elevating or with reduced or limited elevation of estradiol levels.

In one embodiment, the combination of testosterone with anastrozole will relieve symptoms of hormone deficiency in patients in whom elevated estrogen levels are contraindicated.

In one embodiment, the combination of subcutaneous testosterone with anastrozole may offer breast protection and reduce the risk of recurrent disease in breast cancer survivors.

In one embodiment, subcutaneous anastrozole appears to prevent the conversion of DHEA (dehydro-epiandrosterone), an adrenal androgen to estrone, an estrogen that may stimulate breast tissue and elevate with obesity.

DETAILED DESCRIPTION

While testosterone is used in one embodiment of the invention, it will be understood that esters of testosterone may be used such as testosterone propionate, cypionate, enanthate, decanoate, and undecanoate. Herein, with the exception of the claims, the use of the term "testosterone" shall be understood to include testosterone and its esters. The testosterone is used in its crystalline form in one embodiment but it may be used in its noncrystalline or amorphous form in another embodiment. The amount of testosterone in the composition, will be an amount that delivers a pharmaceutically effective serum blood level. In one embodiment, the testosterone is used in implants in an amount of about 30 to 200 mg. In a more particular embodiment, the testosterone is used in an amount of about 50 to 90 mg. As indicated earlier, one or more implants may be used depending on the size, weight and condition of the patient.

Representative examples of aromatase inhibitors useful in accordance with this disclosure include, but are not limited to, anastrozole, letrozole and exemestane. The inhibitor is used in an amount effective to prevent formation of the estradiol from the testosterone. The amount is selected to inhibit the aromatase enzyme will depend on the condition of the patient. More particularly, the inhibitor is used in an amount that is effective in keeping estradiol blood serum levels less than about 54 pg/ml in males and more particularly less than about 45 pg/ml and still more particularly less than about 30 pg/ml. In females, the estradiol blood levels are less than 30 pg/ml in one embodiment. Because the aromatase inhibitor tends to reside in fat tissue, higher doses may be desirable in patients who are obese. In one embodiment the implant contains the inhibitor in an amount of about 1 to 90 mg. In a more particular embodiment, the inhibitor may be used in an amount of about 2 to 50 mg. and in a still more particular embodiment, the inhibitor may be used in the implant in an amount of about 3 to 14 mg.

In accordance with one embodiment of the invention an implant is provided that is able to provide nearly zero order release of the testosterone. In one embodiment the implant is in excess of 90% or 98% active and contains only a small amount of excipient. In one embodiment the implant contains a small amount of a pharmaceutically acceptable lubricant (such as stearic acid) sufficient to facilitate removal of the implant from the pellet forming mold without damage. In another embodiment, to improve the structural integrity of the pellet a small amount of a pharmaceutically acceptable binder is used (e.g., PVP (povidone) (0.2-2 mg) may be used). Neither the stearic acid, nor povidone appears to affect release rate of the active ingredients.

Those skilled in the art will appreciate that the implant can also be formulated as a "matrix" type device, in which an active compound is dispersed in a matrix of carrier material. The carrier material may be either porous or non-porous, solid or semi-solid, and permeable or impermeable to the active compound. Matrix devices may be biodegradable, i.e., they may slowly erode after administration. Alternatively, matrix devices may be nondegradable, and rely on diffusion of the active compound through the walls or pores of the matrix. Other devices may be "reservoir" type, and consist of a central reservoir of active compound surrounded by a rate controlling membrane. The membrane may be porous or non-porous. The release rate often depends only on the surface area of the device. In some cases the sustained release devices are hybrids, having a matrix core surrounded by a membrane.

A number of implant devices are known in the art that may be adopted for use in accordance with this disclosure. For example:

H. Nash, et al., "Steroid Release From Silastic Capsules and Rods" Contraception, 18, 367-394 (1978) discloses both reservoir and matrix implants fashioned from Silastic®, polydimethylsiloxane, for sustained administration of contraceptive steroids. The steroids used are testosterone and testosterone propionate.

Shippy, et al., "Controlled Release of Testosterone Using Silicone Rubber" J. Biomed. Mater. Res., 7, 95-110 (1973) discloses a reservoir device comprising a crystalline testosterone cylinder dipped in Silastic® or a Silastic®/testosterone suspension.

Japanese application J5 9044-310A to Nippon Kayaku discloses a matrix device of a silicone rubber formulation containing a crystalline powdered dissolution assistant (especially a monobasic amino acid, e.g., glycine or alanine, NaCl or mannitol) and an antibiotic or anticancer drug. These devices are reported to achieve a release time of one week to one month.

UK Patent Application 2,167,662A to Dick discloses a matrix implant device in the form of a solid cylinder. The matrix is formed from a hydrophobic polymer such as polypropylene, polyethylene, polyvinyl chloride, ethylvinyl acetate, polystyrene and polymethacrylate, as well as glycerol esters of the glycerol palmitostearate, glycerol stearate and glycerol behenate type.

U.S. Pat. No. 3,948,254 to Zaffaroni discloses a hybrid device comprising a solid matrix drug reservoir encapsulated in a microporous membrane, where the membrane pores are filled with a carrier material.

UK Patent Application 2,154,138A to Roche discloses a hybrid subcutaneous implant using silicone rubber. The device is formed as a substantially hollow cylinder of the silicone rubber, with a core consisting of active ingredients dispersed in a biocompatible, biosoluble polymer which dissolves within days of implantation. The biocompatible, biosoluble polymer is a mixture of high molecular weight polyethylene glycol (PEG) and low molecular weight PEG, for example, PEG 3,000-10,000 with PEG 200-600.

U.S. Pat. No. 5,035,891 to Runkel discloses a subcutaneous implant made by formulating compressed pellets containing a biologically active compound, a solubilizing agent, a solid, hydrophilic, non-toxic polymer sufficient to cause swelling by osmotic pressure after implantation, followed by wrapping the pellet(s) in a rate-controlling membrane which is permeable to the biologically active compound but is impermeable to the solubilizing agent. The implants so obtained are particularly advantageous in a number of respects:

The invention is illustrated in more detail by the following non-limiting example:

Example 1

USP testosterone (50-90 mg) and USP anastrozole (4-12 mg) are mixed with a carrier such as stearic acid (0-4 mg). The mixed ingredients are moulded/compressed in a standard pellet press using 2000 pounds (1 ton) of pressure into cylindrical pellets 3.1 mm diameter.

The individual testosterone/anastrozole pellets are then placed into sealed glass ampoules or standard pharmaceutical 'peel packs.' They are then sterilized using gamma radiation or autoclaved at 121° C. for 40 minutes, steam generator pressure 20-25 psi, autoclave jacket pressure 15-25. Release rate also appears to be independent of compression pressure.

Each sterile implant is supplied in a sealed glass ampoule or standard pharmaceutical peel pack. Do not store above 25° C. Store in the original package.

Clinical Data

Efficacy and Safety of subcutaneous anastrozole/testosterone combination in the elevation of testosterone levels and the prevention of the conversion of testosterone to estradiol is illustrated by the following case presentations:

1. 315 pound, 58 year old male patient previously treated with subcutaneous testosterone replacement therapy (TRT) that presented with an extremely elevated estradiol 8 days following implantation with testosterone pellets (123 pg/mL, optimal range <30 for males). Two weeks following testosterone pellet implantation, two 60 mg testosterone/6 mg anastrozole pellets were implanted into the subcutaneous tissue. One week following implantation of the combination pellets, estradiol measured <30 pg/mL. Testosterone measured 1341 ng/dL. This was confirmed at day 13. Estradiol remained optimal, <30 pg/mL and testosterone measured 1269 ng/dL.
2. 67 year old, 214-pound male treated with subcutaneous TRT with pellet implants presented with an elevated estradiol prior to re-implantation (54 pg/mL). At the time of testosterone pellet implantation, one testosterone 60 mg/anastrozole 6 mg pellet was implanted with 14, 100 mg testosterone pellet implants. Follow up serum levels at one month revealed a therapeutic testosterone levels (842 ng/dL) and estradiol <30 pg·mL. FU serum estradiol level at 2½ months was 45 pg/mL, within range for males (0-54). <30 pg/mL is felt to be optimal. Follow up estradiol at week 15 was <30 pg/mL. Next insert, two testosterone/anastrozole pellet implants will be placed.
3. 55 year old, 63 inch, 135 pound female with a history of invasive breast cancer was treated for symptoms of hormone deficiency with one testosterone 60 mg/anastrozole 6 mg pellet implant in addition to a 55 mg testosterone pellet. Symptoms of androgen/hormone deficiency were relieved and the patient had no side effects from therapy. Ultra-sensitive estradiol measured <7 pg/mL at week 6. Testosterone measured 369 ng/dL. Follow up estradiol at week ten remained low (10 pg/mL) despite a therapeutic testosterone level of 139.6 ng/dL. A second testosterone/anastrozole insert was performed 12 weeks later. Follow up estradiol measures 10 pg/mL (optimal) with a therapeutic testosterone level of 305 ng/dL, consistent with previous results.
4. 50 year old, 71 inch, 210 pound female with a history of metastatic breast cancer, currently on chemotherapy, treated with one testosterone 60 mg/anastrozole 6 mg pellet implant in addition to a 100 mg testosterone pellet implant. Estradiol at day 18 measured <30 pg/mL. Patient noted significant improvement in bone pain from metastatic disease. An additional testosterone 60 mg/anastrozole 6 mg pellet implant was placed 5 weeks after initial insert. Patient experienced further reduction of bone pain. Follow up estradiol remained <30 pg/mL.
5. 50 year old, 62 inch, 146 pound female with a history of invasive breast cancer, was treated with one testosterone 60 mg/anastrozole 6 mg pellet implant in addition to a 55 mg testosterone pellet implant. Serum estradiol at day 7 measured <30 pg/mL.
6. 57 year old, 68 inch, 192 pound female with a history of invasive breast cancer, was treated with one testosterone 60 mg/anastrozole 6 mg pellet implant in addition to a 75 mg testosterone pellet. Serum estradiol at day 13 measured <30 mg/mL. Testosterone measured 165 ng/dL.
7. 58 year old, 64 inch, 160 pound female with a history of breast cancer was treated with one testosterone 60 mg/anastrozole 6 mg pellet implant in addition to an 80 mg testosterone pellet. Serum estradiol at day 24 measured <30 pg/mL and testosterone measured 169 ng/dL.
8. 73 year old, 62.5 inch, 170 pound female with a history of non-invasive (DCIS), bilateral breast cancer, was treated with one testosterone 60 mg/anastrozole 6 mg pellet implant in addition to a 100 mg testosterone pellet implant. Serum estradiol at day 13 measured <30 pg/mL and testosterone measured 290 ng/dL.
9. 56 year old, 65.5 inch, 220 pound female with a history of breast cancer, was treated with one testosterone 60 mg/anastrozole 6 mg pellet implant in addition to a 100 mg testosterone pellet implant. Estradiol at day 25 measured <30 pg/mL and testosterone measured 247 ng/dL.
10. 53 year old, 59 inch, 183 pound female with a history of invasive breast cancer treated with chemotherapy was treated with one testosterone 60 mg/anastrozole 6 mg pellet implant in addition to a 100 mg testosterone pellet implant. Serum estradiol at day 7 measured <30 pg/mL, estrone <10 pg/mL and testosterone measured 220 ng/dL. Previously she had been unable to tolerate 'low dose' (0.5 mg twice weekly) oral anastrozole, complaining of severe hot flashes, night sweats "all through the night", and headaches. She had discontinued the oral anastrozole. She experienced no side effects with the subcutaneous anastrozole with testosterone pellet implant.
11. 54 year old, 67 inch, 145 pound female with a history of non-invasive breast cancer (DCIS), was treated with one testosterone 60 mg/anastrozole 6 mg pellet implant in addition to a 55 mg testosterone pellet implant. Serum 'sensitive' estradiol at day 7 measured 25 pg/mL. Serum estrone also remained low, 22 pg/mL.

12. 64 year old, 144 pound female with a history of breast cancer, was treated with one testosterone 60 mg/anastrozole 6 mg pellet implant in addition to a 55 mg testosterone pellet implant. Serum estradiol measured <10 pg/mL and testosterone measured 313.9 ng/dL at week one.

13. 78 year old, 140 pound female with a history of breast cancer, was treated with one testosterone 60 mg/anastrozole 6 mg pellet implant in addition to a 55 mg testosterone pellet implant. Day 9, serum estrone measured <10 pg/mL, estriol <0.10 and testosterone 300 ng/dL.

14. 45 year old, 66 inch, 135 pound female with a history of breast cancer, was treated with one testosterone 60 mg/anastrozole 6 mg pellet implant in addition to a 55 mg testosterone pellet implant. Serum estradiol at week one measured <30 pg/mL, estrone <10 pg/mL with a therapeutic testosterone of 136 ng/dL.

15. 51 year old, 154 pound female with a history of metastatic breast cancer, was treated with one testosterone 60 mg/anastrozole 6 mg pellet implant in addition to a 100 mg testosterone pellet implant. Day 18, serum estradiol measured <10 ng/dL, total estrogens <1.0 ng/dL and testosterone 404 ng/dL.

16. 48 year old, 66 inch, 155 pound female with a history of invasive breast cancer, was treated with one testosterone 60 mg/anastrozole 6 mg pellet implant in addition to a 100 mg testosterone pellet implant. Serum estradiol at week one measured <30 pg/mL with a therapeutic testosterone of 232 ng/dL.

17. 61 year old, 64 inch, 160 pound female with a history of invasive breast cancer 15 years prior treated with chemotherapy and tamoxifen treated with one testosterone 60 mg/anastrozole 6 mg pellet implant in addition to a 75 mg testosterone pellet implant. Serum estradiol at week one measured <30 pg/mL, Estrone was 15 pg/mL (optimal) with a therapeutic testosterone of 191 ng/dL.

18. 67 year old, 67 inch, 170 pound female with a history of DCIS, ductal carcinoma in situ (non invasive breast cancer), treated with lumpectomy and radiation therapy. The patient with one testosterone 60 mg/anastrozole 6 mg pellet implant in addition to a 65 mg testosterone pellet implant. Serum estradiol measured <10 pg/mL, Estrone 4.3 pg/mL (3-32 pg/mL post men), with a therapeutic testosterone level of 453 ng/dL.

19. 47 year old, 210 pound female with a history of breast cancer, was treated with one testosterone 60 mg/anastrozole 6 mg pellet implant in addition to a 100 mg testosterone pellet implant. Day 12, serum estradiol measured 41 pg/mL (not considered elevated, but slightly above post menopausal levels) with a therapeutic testosterone of 338 ng/dL. Patient felt great. Estradiol was remeasured at week 4, and testosterone was 460 ng/dL, and estradiol was <30 pg/mL, FSH 50.2.

While the invention has been illustrated by several expressions of several embodiments, and enablements, and applications, thereof, the invention is defined by the appended claims and is not limited to the specific examples. Numerous variations, modifications, and substitutions are possible without departing from the scope of the invention as defined in the appended claims. It will be understood that the foregoing description is provided by way of example, and that other modifications may occur to those skilled in the art without departing from the scope and spirit of the appended Claims.

What is claimed is:

1. An implant comprising a mixture of an amount of testosterone or an ester thereof and an amount of aromatase inhibitor in a weight ratio of testosterone or an ester thereof to aromatase inhibitor of 5:1 to 30:1, wherein the mixture forms a single implant with continuous delivery and zero order release of the testosterone or ester thereof and the aromatase inhibitor for a period of at least 30 days.

2. The implant of claim 1, wherein the aromatase inhibitor is selected from the group consisting of anastrozole, letrozole, and exemestane.

3. The implant of claim 1, further comprising an amount of a pharmaceutically acceptable excipient.

4. The implant of claim 1, wherein the implant is a sustained release, subcutaneous implant.

5. The implant of claim 1, wherein the amount of testosterone is about 30 mg to 200 mg and the amount of aromatase inhibitor is about 1 mg to 90 mg.

6. The implant of claim 1, wherein the amount of testosterone or an ester thereof and the amount of aromatase inhibitor is a weight ratio of testosterone or an ester thereof to aromatase inhibitor of about 15:1.

7. The implant of claim 1, wherein the amount of testosterone or an ester thereof and the amount of aromatase inhibitor are released into the blood at a controlled rate.

8. The implant of claim 3, wherein the excipient comprises a lubricant, a binder, or a combination thereof.

9. The implant of claim 1, wherein the amount of aromatase inhibitor provides less than 54 pg/ml estradiol level in the blood.

10. The implant of claim 3, wherein the amount of excipient is less than about 5% by weight based on composition weight.

11. The implant of claim 1, wherein the aromatase inhibitor comprises anastrozole.

12. The implant of claim 1, wherein the amount of testosterone or an ester thereof is about 60 mg and the amount of aromatase inhibitor is about 4 mg.

13. An implant comprising a mixture of an amount of testosterone or an ester thereof and an amount of aromatase inhibitor in a weight ratio of testosterone or an ester thereof to aromatase inhibitor of about 5:1 to 30:1, wherein the amount of testosterone or an ester thereof and the amount of aromatase inhibitor are continuously delivered at a zero order release for a period of at least 30 days, and wherein the amount of aromatase inhibitor prevents formation of estradiol from the testosterone and provides less than 54 pg/ml estradiol level in the blood.

14. The implant of claim 13, wherein the implant is a sustained release, subcutaneous implant.

15. The implant of claim 13, further comprising a pharmaceutically acceptable excipient.

16. The implant of claim 13, wherein the aromatase inhibitor is selected from the group consisting of anastrozole, letrozole, and exemestane.

17. The implant of claim 13, wherein the amount of testosterone or an ester thereof is about 30 mg to 200 mg and the amount of aromatase inhibitor is about 1 mg to 90 mg.

18. The implant of claim 13, wherein the weight ratio of testosterone or an ester thereof to aromatase inhibitor is about 15:1.

19. The implant of claim 1, wherein the aromatase inhibitor comprises letrozole.

* * * * *